(12) United States Patent
Scanlin

(10) Patent No.: US 11,006,877 B1
(45) Date of Patent: May 18, 2021

(54) SYSTEM AND METHOD FOR IDENTIFYING AND ATTENUATING MENTAL HEALTH DETERIORATION

(71) Applicant: Navigate Labs, LLC, Milwaukee, WI (US)

(72) Inventor: Joseph Scanlin, Milwaukee, WI (US)

(73) Assignee: Navigate Labs, LLC, Milwaukee, WI (US)

( * ) Notice: Subject to any disclaimer, the term of this patent is extended or adjusted under 35 U.S.C. 154(b) by 0 days.

(21) Appl. No.: 16/700,344

(22) Filed: Dec. 2, 2019

(51) Int. Cl.
*A61B 5/16* (2006.01)
*G06N 20/00* (2019.01)
*G06F 3/01* (2006.01)
*H04W 4/90* (2018.01)
*G10L 25/63* (2013.01)

(52) U.S. Cl.
CPC ............... *A61B 5/165* (2013.01); *G06F 3/01* (2013.01); *G06N 20/00* (2019.01); *G10L 25/63* (2013.01); *H04W 4/90* (2018.02); *G06F 2203/011* (2013.01)

(58) Field of Classification Search
CPC ............ A61B 5/16; A61B 5/165; A61B 5/168
USPC .................................................. 434/236, 238
See application file for complete search history.

(56) References Cited

U.S. PATENT DOCUMENTS 9,418,390 B2 * 8/2016 Chun ..................... G06Q 50/01
9,928,462 B2 * 3/2018 Lee ........................ G06N 7/005

\* cited by examiner

*Primary Examiner* — Robert J Utama
(74) *Attorney, Agent, or Firm* — Dickinson Wright, PLLC; Stephen A. Mason; Jonathan H. Harder

(57) ABSTRACT

A method for determining a state of mind of a user may include receiving one or more strings of characters composed by the user, and determining, by a processing device, the state of mind of the user by processing the one or more strings of characters. The processing of the one or more strings of characters may include identifying similarities of the one or more strings of characters with other strings of characters indicative of the state of mind. The method may also include determining, based on the one or more strings of characters, a severity of the state of mind of the user.

17 Claims, 7 Drawing Sheets

SYSTEM AND METHOD FOR IDENTIFYING AND ATTENUATING MENTAL HEALTH DETERIORATION

TECHNICAL FIELD

This disclosure relates to computational linguistics. More specifically, this disclosure relates to a system and method for using computational linguistics to identify and attenuate mental health deterioration.

BACKGROUND

People have struggled with depression since the beginning of recorded history. Anthropological studies suggest that hunter-gatherer groups exhibited similar depressive symptoms as the modern-day population does, with similar reactions to similar types of issues, and similar resulting biological manifestations. Depression, anxiety, and other deteriorated states of mental health are often treated in similar fashion as discrete illnesses, where diagnoses and resulting treatments are primarily predicated on whether or not an observer, or a mechanical method of observation, suggests a person is in a specific state of mind: depressed or not depressed. However, depression is not a typical illness. Depression is a probabilistic tendency to exhibit any of a wide range of interrelated symptoms in response to environmental adversity. Simply stated, depression is more akin to an oscillation between two mental poles: happy and sad.

SUMMARY

Representative embodiments set forth herein disclose various techniques for enabling a system and method for electronic assignment of issues based on measured and/or forecasted capacity of human resources.

In one embodiment, a method for determining a state of mind of a user may include receiving one or more strings of characters composed by the user, and determining, by a processing device, the state of mind of the user by processing the one or more strings of characters. The processing of the one or more strings of characters may include identifying similarities of the one or more strings of characters with other strings of characters indicative of the state of mind. The method may also include determining, based on the one or more strings of characters, a severity of the state of mind of the user. In some embodiments, an intervention may be performed electronically, in real-time or near real-time, based on the state of mind of the user and/or the severity of the state of mind of the user.

In some embodiments, a tangible, non-transitory computer-readable medium storing instructions that, when executed, cause a processing device to perform one or more of the operations described above. In some embodiments, a system may include a memory storing instructions and a processor communicatively coupled to the memory. The processor may execute the instructions to perform one or more of the operations described above.

Other technical features may be readily apparent to one skilled in the art from the following figures, descriptions, and claims.

BRIEF DESCRIPTION OF THE DRAWINGS

For a detailed description of example embodiments, reference will now be made to the accompanying drawings in which.

NOTATION AND NOMENCLATURE

Figure 1:
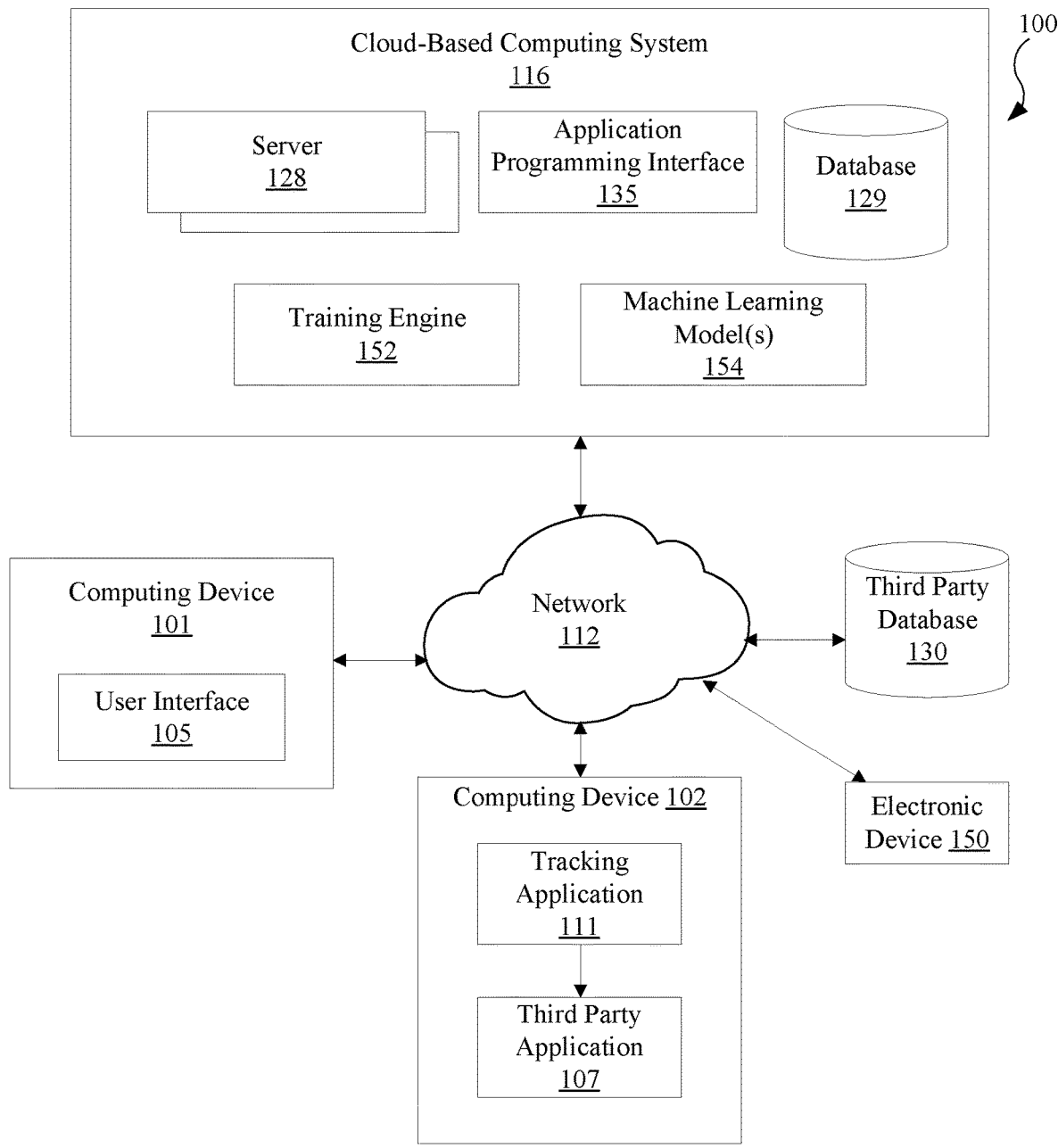
FIG. 1 illustrates a high-level component diagram of an illustrative system architecture according to certain embodiments of this disclosure.

Various terms are used to refer to particular system components. Different entities may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer or section from another region, layer or section. Terms such as "first," "second," and other numerical terms, when used herein, do not imply a sequence or order unless clearly indicated by the context. Thus, a first element, component, region, layer or section discussed below could be termed a second element, component, region, layer or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more"

when used with a list of items means there may be one item or any suitable number of items exceeding one.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), solid state drives (SSDs), flash memory, or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

DETAILED DESCRIPTION

Approaches to identifying a trajectory of a mental health event typically take form in one of two ways: (1) human personality diagnoses conducted by an expert in an attempt to identify schema using theoretical and practical knowledge, and (2) assessments built on findings from individual cases and analyses that are presented in the form of an encouraged literary exercise or a questionnaire that can be applied to a wide audience. However, these approaches have several shortcomings. For example, ignoring the idea that adaptive failures run along a continuum may contribute to these approaches being less effective, which in return, promotes an imbalanced or inaccurate care-delivery regimen. A negligible portion of the population remains in a single, consistent state of happiness. Moreover, the psychoanalytic perspective of these approaches view mental disorders as one large process that is amendable to a single treatment. These approaches void the possibility for real-time identification, thereby making it near impossible to intervene at an opportune time.

Accordingly, embodiments of the present disclosure may refer to identifying a mental state of a user and a severity of the mental state and performing an intervention in real-time or near real-time. Real-time or near real-time may refer to performing an action (e.g., intervention, transmitting data (text, characters, words, video, etc.) within a fraction of a second. In some embodiments, real-time text may refer to text that is transmitted while it is being typed or created, with characters being sent immediately once typed, and also displayed and/or processed immediately to any receiving computing device. In some embodiments, real-time messaging may refer to messages that are completely composed and transmitted immediately (within a fraction of a second) upon a user selecting to send the message or some triggering factor (e.g., a threshold delay period where the user stops entering text, the user selects to save the message, etc.).

Computational linguistics may refer to an interdisciplinary field concerned with statistical/rule-based processing of natural language through computation. In some embodiments, computational linguistics may be used for accurate and effective personality and health analysis for the purpose of identifying a particular state of mind and/or severity of the state of mind and quickly applying an appropriate intervention. In some embodiments, artificial intelligence techniques may be used, such as machine learning models implementing neural networks, or the like, that are trained to receive strings of characters entered or spoken by the user and determine a state of mind of the user, determining a severity of the state of mind of the user, and/or perform an intervention based on the state of mind of the user and/or the severity of the state of mind of the user.

The machine learning models may be trained based on input from numerous users. For example, a user may use an application to enter text or speak words and may specify their state of mind and the severity of their state of mind at the time at which they entered the text or spoke the words. The state of mind may be any suitable state of mind such as happy, sad, mad, frustrated, playful, tired, worried, anxious, etc. Accordingly, the machine learning models may be trained with a "ground truth" or baseline of a correlation of the way in which the users type or speak and their mental states and/or severities of their mental states. In some embodiments, a corpus of training data including strings of characters of users and labeled with states of mind and/or severities of states of mind of the user when the strings of characters were created. The corpus of training data may be obtained from one or more repositories that harbor mental states of users. The machine learning models may perform natural language processing and distributional semantics to process written language and/or spoken language historically and/or in real-time to assess the state of mind and/or severity of the state of mind. Further, the disclosed techniques may cause a minor to major intervention predicated on the mental state and/or severity of the mental state of the user.

In some embodiments, the interventions may be performed in a digital realm, a physical environment realm, and/or the like. For example, the interventions may include: (i) causing a color of a display screen of a computing device of the user to be altered, (ii) transmitting a first message to a computing device of a third party, where the first message recommends contacting the user, (iii) causing a prompt to be presented on the computing device of the user, where the prompt recommends the user stand up, walk, or briefly meditate, (iv) causing the computing device of the user to connect to a telephonic-health service, (v) transmitting a second message to an emergency service, where the second message indicates an event is likely to occur, and/or (vi) causing an electronic device to change a parameter (e.g., smart light changes color emitted, brightness, or both; smart thermostat changes temperature; speaker plays music; speaker emits a phrase).

In some embodiments, the change in the state of mind of the user and/or the severity of the state of mind of the user over time may be tracked. If the severity of the state of mind changes a threshold amount (e.g., 2-8 levels) in less than a threshold amount of time (e.g., less than an hour, a few hours, a day, a few days, etc.), then a major intervention may be performed. For example, if the user is in a sad state of mind and the severity changes from a 1 to a 9 within a day, then a major intervention may be performed. If the severity of the state of mind changes less than the threshold amount (e.g., 1 level) in a threshold amount of time (e.g., more than an hour, a few hours, a day, a few days, etc.), then a minor intervention may be performed. It should be noted that the threshold amount of severity levels and the severity amount of time may be configurable to any suitable values.

The disclosed embodiments may provide various technical advantages. For example, the disclosed embodiments receive data from multiple different data feeds (e.g., any application executed on the computing device of the user where the user enters text: email applications, word processing applications, spreadsheet applications, note applications, social media applications, internet websites, etc.). The disclosed techniques may also quickly and efficiently process the respective data individually or in combination to determine a state of mind of a user and/or a severity of the user to perform an intervention in real-time or near real-time to intervene at an opportune moment. Intervening at the opportune moment may prevent a user from performing a harmful act to their self or others and/or may alter the mental state of the user to change their mental state and/or lessen/increase the severity of their mental state. The disclosed embodiments may improve a user's experience with a computing device due to the interventions being performed at selected moments where the users are feeling particularly sad, depressed, and/or frustrated. The interventions may enable a computing device of a cloud-based computing system to control various other computing device.

FIG. 1 illustrates a high-level component diagram of an illustrative system architecture 100 according to certain embodiments of this disclosure. In some embodiments, the system architecture 100 may include a computing device 101, a computing device 102, a cloud-based computing system 116, an electronic device 150, and/or a third party database 130 that are communicatively coupled via a network 112. As used herein, a cloud-based computing system refers, without limitation, to any remote or distal computing system accessed over a network link. Each of the computing device 101, computing device 102, and electronic device 150 may include one or more processing devices, memory devices, and network interface devices.

The network interface devices of the computing devices 101 and 102 and the electronic device 150 may enable communication via a wireless protocol for transmitting data over short distances, such as Bluetooth, ZigBee, near field communication (NFC), etc. Additionally, the network interface devices may enable communicating data over long distances, and in one example, the computing device 101 and/or 102 and the electronic device 150 may communicate with the network 112. Network 112 may be a public network (e.g., connected to the Internet via wired (Ethernet) or wireless (WiFi)), a private network (e.g., a local area network (LAN), wide area network (WAN), virtual private network (VPN)), or a combination thereof.

The computing device 101 may be any suitable computing device, such as a laptop, tablet, smartphone, or computer. The computing device 101 may include a display that is capable of presenting a user interface 105. The computing device 101 may be operated by a third party (e.g., a spouse, a family member, a son, a relative, a sponsor, an emergency service employee, or any suitable person besides a user of the computing device 102). The user interface 105 may be implemented in computer instructions stored on a memory of the computing device 101 and executed by a processing device of the computing device 101. The user interface 105 may be a stand-alone application that is installed on the computing device 101 or may be an application (e.g., website) that executes via a web browser. The user interface 105 may present various screens, notifications, and/or messages to a user. The screens, notifications, and/or messages may encourage the user of the computing device 101 to contact the user of the computing device 102 by emailing them, text messaging them, and/or calling them. The encouragement may specify the user of the computing device 101 to inquire how the user of the computing device 102 is feeling and attempt to cheer up the user of the computing device 102. Further, the notification may indicate to an emergency service employee (e.g., dispatcher, police officer, emergency medical technician, etc.) that a potentially harmful event may occur based on the determined mental state and/or severity of mental state of the user of the computing device 102.

The computing device 102 may execute a third party application 107. The third party application 107 may be implemented in computer instructions stored on the one or more memory devices of the computing device 102 and executable by the one or more processing devices of the computing device 102. The third party application 107 may be any suitable software application that is capable of receiving textual input and/or video input. For example, the third party application 107 may be a word processing application, spreadsheet application, slideshow application, software development application, animation application, video editing application, note taking application, social media application, social media website, web browser, or the like. The third party application 107 may interface with an application programming interface 135 (API) of the cloud-based computing system 116. For example, the API 135 may be used to provide a user interface element (e.g., a text input box and/or field) that is embedded in a screen of the third party application 107. The third party application 107 may be a bot that is implemented by a virtual meeting platform or any suitable web site that allows users to implement text and/or video of users talking in real-time. A bot may refer to a computer program that performs automated tasks. The automated tasks may include transmitting text to the cloud-based computing system 116, extracting text from spoken words in a video and transmitting the text to the cloud-based computing system 116, or some combination thereof.

The computing device 102 may also execute a tracking application 111. The tracking application 111 may be implemented in computer instructions stored on the one or more memory devices of the computing device 102 and executable by the one or more processing devices of the computing device 102. The tracking application 111 may be provided by the cloud-based computing system 116. The tracking application 111 may be a keystroke analyzer that monitors any program the user uses to enter text. The tracking application 111 may transmit the text represented by the keystrokes the user performed in any suitable application to the cloud-based computing system 116. The tracking application 111 may monitor an amount of time the user is actively using the third party application 107 and transmit that amount of time to the cloud-based computing system 116. The amount of time the user uses the third party application 107 may be considered as a factor when determining a mental state of the user and/or a severity of the mental state of the user.

In some embodiments, the cloud-based computing system 116 may include one or more servers 128 that form a distributed, grid, and/or peer-to-peer (P2P) computing architecture. Each of the servers 128 may include one or more processing devices, memory devices, data storage, and/or network interface devices. The servers 128 may be in communication with one another via any suitable communication protocol. The servers 128 may determine the mental state of the user and/or a severity of the mental state of the user based on strings of characters entered by the user or extracted from words spoken by the user in a video. The servers 128 may use one or more machine learning models 154 trained to determine the mental state of the user and/or a severity of the mental state of the user. The server 128 and/or the machine learning models 154 may determine to perform an intervention based on the mental state of the user and/or a severity of the mental state of the user.

In some embodiments, the cloud-based computing system 116 may include a training engine 152 and/or the one or more machine learning models 154. The training engine 152 and/or the one or more machine learning models 154 may be communicatively coupled to the servers 128 or may be included in one of the servers 128. In some embodiments, the training engine 152 and/or the machine learning models 154 may be included in the computing device 101 and/or 102.

The one or more of machine learning models 154 may refer to model artifacts created by the training engine 152 using training data that includes training inputs and corresponding target outputs (correct answers for respective training inputs). The training engine 152 may find patterns in the training data that map the training input to the target output (the answer to be predicted), and provide the machine learning models 154 that capture these patterns. The set of machine learning models 154 may comprise, e.g., a single level of linear or non-linear operations (e.g., a support vector machine [SVM]) or a deep network, i.e., a machine learning model comprising multiple levels of non-linear operations. Examples of such deep networks are neural networks including, without limitation, convolutional neural networks, recurrent neural networks with one or more hidden layers, and/or fully connected neural networks.

In some embodiments, the training data may include inputs of words (strings of characters), types of words, number of words, misspelled words, times and/or dates when the words are entered, phrases, facial expressions, vital signs, financial information, health related information, or some combination thereof and correlated outputs of a mental state and/or a severity of the mental state. The training data may be obtained from a sample of people using a computer application to enter strings of characters (e.g., a digital diary) describing how they are feeling or what they are doing and also inputting their mental state and/or how severe their mental state is. For example, the text may be "I am very sad" which may be correlated with a sad mental state having a high severity (e.g., level 7-10). In other instances, the user may or may not use certain pronouns at a certain ratio to other types of words, may misspell words, may use certain types of words at a certain ratio to other types of words, may use the computer application at a certain time of day, make certain facial expressions, and the like that is correlated with the mental state and/or severity of mental state specified by the user. The machine learning models 154 may be trained to use natural language processing and semantic distribution to recognize the strings of characters received from the computing device 102. In cases where videos and/or images are received, the machine learning models 154 may be trained to use facial character recognition, object character recognition, and/or facial expression detection to determine what type of facial expression the user is making.

The natural language processing may use if-then rules, and/or statistical models. The statistical models may make soft, probabilistic decisions based on attaching real-valued weights to each input feature. Such models may have the advantage that they may express relative certainty of many different possible answers rather than just one, thereby producing more reliable results when such a model is included as a component of a larger system. The learning procedures used during machine learning natural language processing may automatically focus on the most common cases. Further, automatic learning procedures may make use of statistical-inference algorithms to produce models that are robust to unfamiliar input (e.g. containing words or structures that have not been seen before) and to erroneous input (e.g. with misspelled words or words accidentally omitted). Further, systems based on automatically learning the rules can be made more accurate simply by supplying more input data. The natural language processing may use various syntax techniques, such as grammar induction, lemmatization, morphological segmentation, part-of-speech tagging, parsing, sentence breaking, stemming, word segmentation, and/or terminology extraction. Also, the natural language processing may use various semantics, such as lexical semantics, distributional semantics, machine translation, named entity recognition, natural language generation, natural language understanding, optical character recognition, question answering, recognizing textual entailment, relationship extraction, sentiment analysis, topic segmentation, word sense disambiguation, and the like. Further, natural language processing may perform the following discourse techniques: automatic summarization, coreference resolution, discourse analysis, and the like. The natural language processing may also perform the following speech techniques: speech recognition, speech segmentation, text-to-speech, dialogue, and the like.

The machine learning models 154 may be trained with the training data to perform an intervention based on the determined mental state and/or severity of the mental state. For example, if the mental state of the user is sad and the severity is at a threshold level (e.g., 7-10), then a major intervention may be performed, such as contacting emergency services to notify that a harmful or bad event may occur soon. If the mental state of the user is sad and the severity is below the threshold level (e.g., less than a 7), then a minor intervention may be performed.

In some embodiments, the trained machine learning model 154 may receive an input of strings of characters (e.g., entered by the user using the third party application 107 and/or extracted from spoken words in a video) and/or facial images depicting facial expressions, and output the mental state of the user and/or the severity of the user. In some embodiments, the machine learning models 60 are linked such that their outputs are used as inputs to one another. For example, the mental state output by a first machine learning model 154 may be input into a second machine learning model 154 that outputs the severity of the mental state.

In some embodiments, the cloud-based computing system 116 may include a database 129. The third party database 130 may store data pertaining to observations determined by the machine learning models 154. The observations may pertain to the mental state and/or severity of mental states of certain users. The observations may be stored by the database 129 over time to track the degradation and/or improvement of the mental state of the user. Further, the observations may include indications of which types of interventions are successful in improving the mental state and/or lowering the severity of a mental state when a user has a particular mental state at a particular severity. In some embodiments, the actual text received from the computing device 102 may not be stored by the database 129. The database 130 may store data pertaining to a corpus of strings of characters and correlated mental states and/or severity levels of the mental states of users based on the observations. The training data used to train the machine learning models 154 may be stored in the database 129.

In some embodiments, the cloud-based computing system 116 may include an application programming interface (API) 135 that communicatively couples to the third party database 130 via the network 112. The API 135 may be implemented as computer instructions stored on one of the servers 128 and executed by a processing device of one of the servers 128. The third party database 130 may store data pertaining to a corpus of strings of characters and correlated mental states and/or severity levels of the mental states of users. In some embodiments, the third party database 130 may not store the actual text entered by users. For example, the entity may be a police department, a medical facility, a psychiatric facility, a research facility, or the like. The data in the third party database 130 may be harvested from computing devices of users of the entity using tracking applications and/or survey applications. The API 135 may extract the data from the third party database 130 to perform the techniques disclosed herein. The training data used to train the machine learning models 154 may be stored in the third party database 130.

Figure 2:
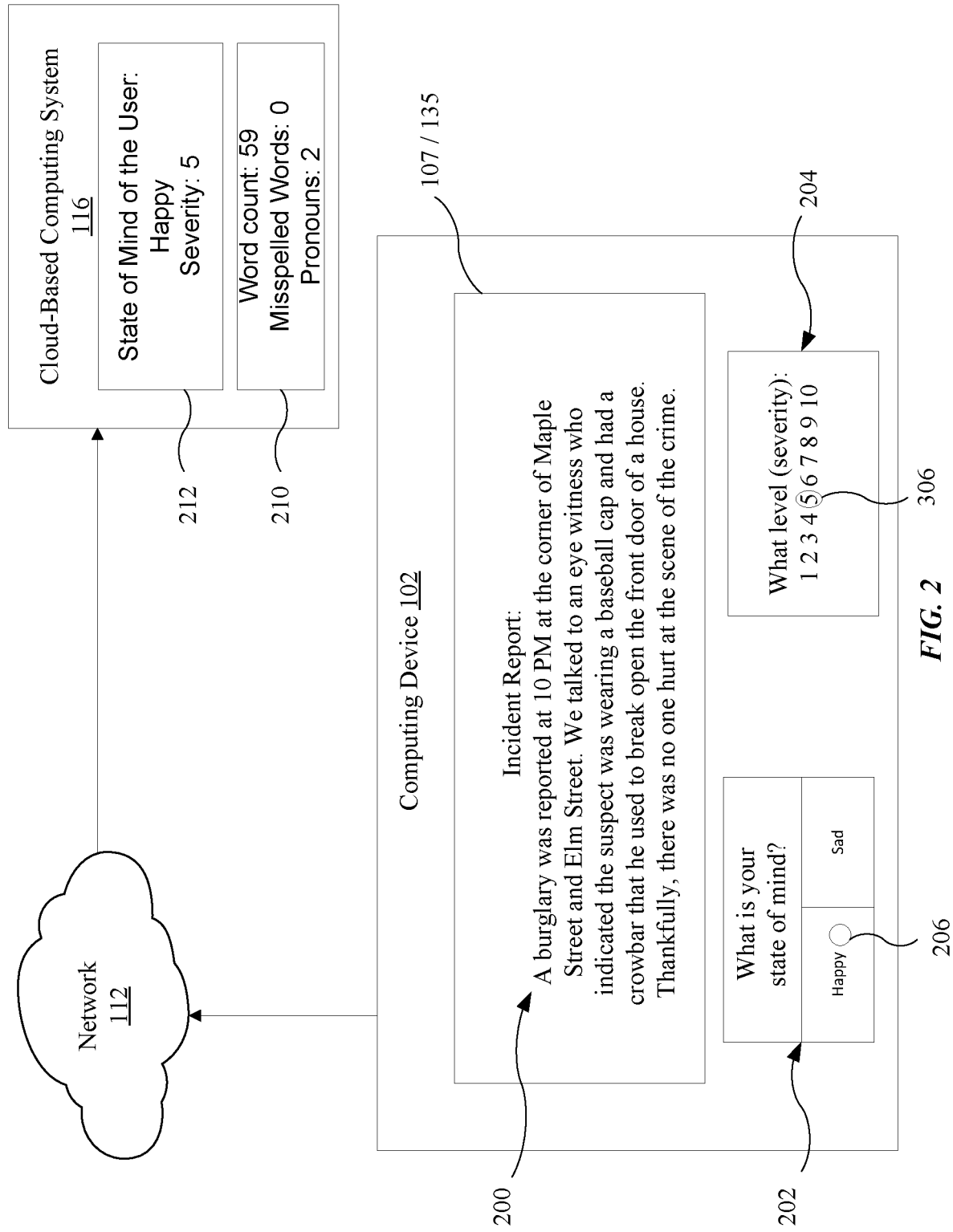
FIG. 2 illustrates an example block diagram of a cloud-based computing system receiving text, indications of a state of mind of a user, and a severity of the state of mind according to certain embodiments of this disclosure.

FIG. 2 illustrates an example block diagram for a cloud-based computing system 116 receiving text 200, indications of a state of mind 202 of a user, and a severity 204 of the state of mind of the user according to certain embodiments of this disclosure. As depicted, the user is using the computing device 102 and a third party application 107 that may be implementing a text input box of the API 135. The user in the depicted example may be a police officer entering an incident report. The user typed "A burglary was reported at 10 PM at the corner of Maple Street and Elm Street. We talked to an eye witness who indicated the suspect was wearing a baseball cap and had a crowbar that he used to break open the front door of a house. Thankfully, there was no one hurt at the scene of the crime." The user also selected (represented by circle 206) a "Happy" state of mind 202, and a severity 204 of level 5 in a range of 1-10 (e.g., 1 being a minimum severity level and 10 being a maximum severity level). The text 200, the state of mind 202, and/or the severity 204 may be transmitted to the cloud-based computing system 116 via the network 112.

The cloud-based computing system 116 may receive the text 200, the state of mind 202 of the user at the time the user entered the text 200, and/or the severity 204 of the state of mind 202 of the user. The cloud-based computing system may use the text 200, the state of mind 202 of the user at the time the user entered the text 200, and/or the severity 204 of the state of mind 202 of the user to train a machine learning model. For example, the machine learning model may use the text to identify a pattern between the state of mind 202 and/or the severity 204 of the state of mind with the types of words included in the text, a number of words included in the text 200, a number of misspelled words in the text 200, a number of pronouns in the text 200, a ratio of pronoun count to other words in the text 200, a ratio of certain types of words to other certain types of words in the text 200, and so forth.

For example, if the user does not use the pronoun "I", then the user may be trying to distance their self from a certain event described in the text 200 and that may be a sign that the user is sad/guilty/mad/regretful about the event. If the user uses certain gracious and/or celebratory words like "thankfully", then the user may be relieved/happy/satisfied/excited about the event they are describing. As depicted, the user entered "We" when referring to talking to an eye witness, so the user is associating their self and someone else with the event. Further, the user used the word "Thankfully" in the text 200, so the user is expressing gratefulness associated with the event.

Also, the user entered 59 words, misspelled 0 words, and used two pronouns ("we" and "who"), as depicted in box 210. Further, the user indicated their state of mind 202 is "Happy" and the severity level 204 of their happiness is a 5. The cloud-based computing system 116 may use this information with the text 200 to train the machine learning models 154 that these properties (e.g., word count, number of misspelled words, number of pronouns, ratio of certain words to other certain words, celebratory or gracious words, regretful words, and the like) of the strings of characters in the text 200 (which may be entered by the user or extracted from spoken words in a video of the user) are indicative of a pattern correlated with a "Happy" state of mind 202 and a severity 204 of a level 5 for the state of mind 202 (shown in box 212).

It should be noted that numerous users may use numerous computing devices 102 to enter any suitable text 200 with their state of mind 202 at the time they entered the text and/or the severity 204 of their state of mind 202 when the entered the text 200. The text 200 entered by the multiple users, along with the associated state of minds 202 and/or severity 204 of the state of mind 202, may be used as training data to train the machine learning models 154.

Figure 3:
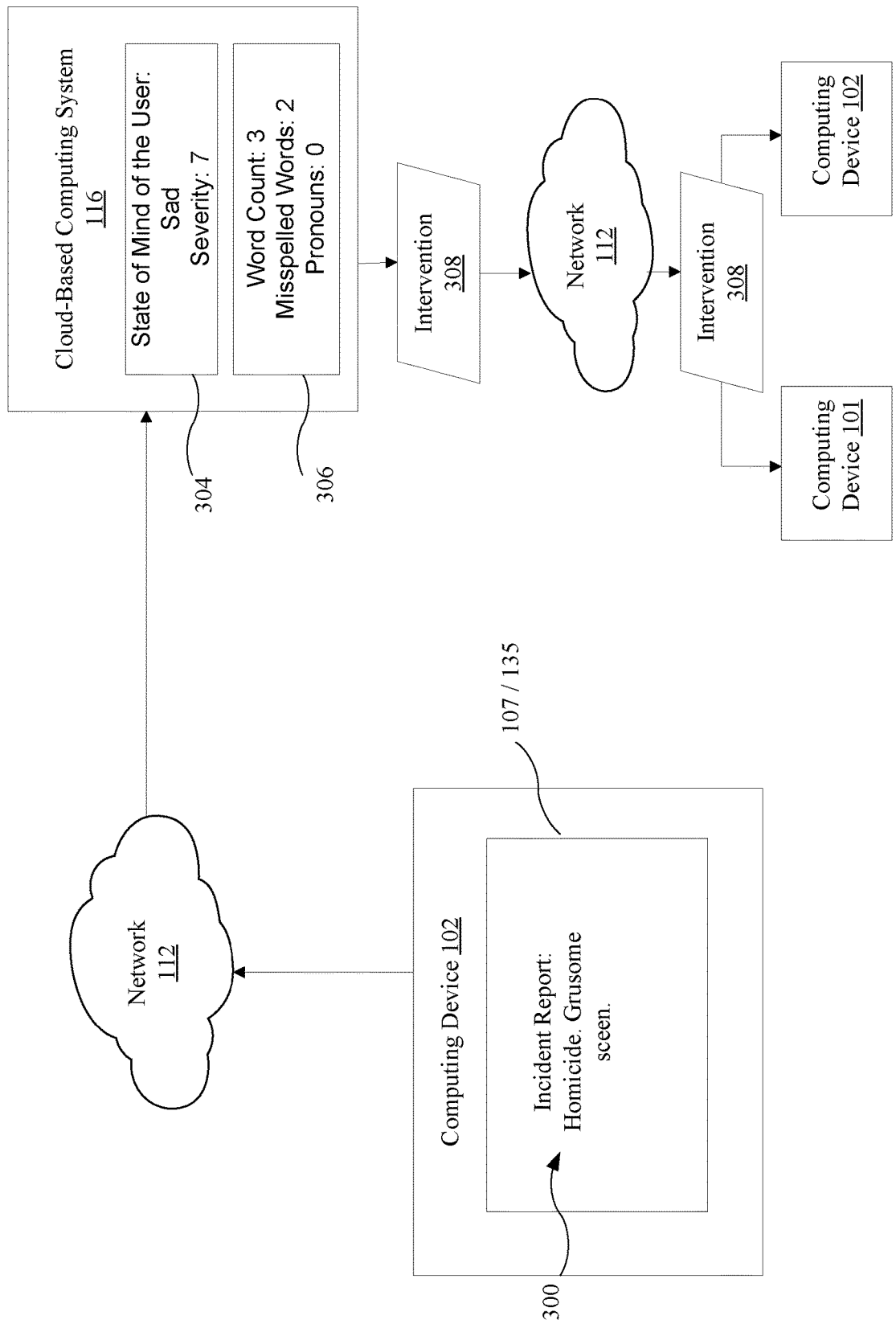
FIG. 3 illustrates an example block diagram of receiving additional text of the user according to certain embodiments of this disclosure.

FIG. 3 illustrates an example block diagram of receiving additional text 300 of the user according to certain embodiments of this disclosure. As depicted, the user is using the computing device 102 and a third party application 107 that may be implementing a text input box of the API 135. In the depicted example, it should be understood that the machine learning models 154 of the cloud-computing device 116 may be trained based on the training data discussed above (e.g., with reference to FIGS. 1 and 2). The user of the computing device 102 is also a police officer filling out an incident report. The user typed "Homicide. Grusome Sceen." The text 300 may be transferred in real-time as the user types each letter or after the user completes the text 300 and selects to save the text 300 or a threshold period of time elapses since the user's last keystroke.

The cloud-based computing system 116 may input the received text 300 into the trained machine learning models 154. The trained machine learning models 154 may determine that the text 300 includes 3 words (very low) total, 2 misspelled words ("Grusome" and "sceen"), and 0 pronouns, as shown in box 306. Accordingly, the misspelling of words may be determined to be correlated with the user using a drug or mood altering substance (e.g., alcohol, marijuana, etc.) to try to enhance their mood. The low word count indicates the user is not very interested in talking about the event they are describing. The lack of pronouns may indicate that the user is distancing their self from the event. Further, the substance of the event (e.g., "Homicide") and the description of the event (e.g., "Grusome sceen") may indicate the user experienced some type of trauma. Further, the strings of characters in the text 300 may be compared to other strings of characters to identify similarities of the strings of characters with the other strings of characters that are indicative of a particular state of mind. For example, the string of characters "sad" may indicate the state of mind "sad". Based on the foregoing, the machine learning models 154 may be trained to output a determination that the user has a "Sad" state of mind and a severity of "7".

Accordingly, the cloud-based computing device 116 may perform an intervention 308. The intervention 308 may be transmitted by the cloud-based computing system 116 through the network to the computing device 101, the computing device 102, or both. For example, the intervention 308 may be a notification to the user of the computing device 102 to take a break, take a walk, breathe deeply, meditate, or the like. In another example, the intervention 308 may include notifying the user of the computing device 101 to reach out to the user of the computing device 102 to check on them. Accordingly, one or more interventions may be performed at an opportune time (e.g., in real-time) when a poor state of mind of the user is detected.

In some embodiments, if the user of the computing device 102 in FIG. 3 is the same as the user of the computing device 102 in FIG. 2, and the amount of time between incident reports is than a threshold amount of time, then a more sever intervention may be performed. For example, if the user entered text 300 one day after the user entered text 200, then the intervention 308 may include contacting emergency services and/or a manager of the user to indicate that a harmful event may occur to the user or to someone else. If the severity of the state of mind of the user gradually gets worse over a period of time, the type of interventions may increase from minor to major over that period of time depending on the severity level.

Figure 4:
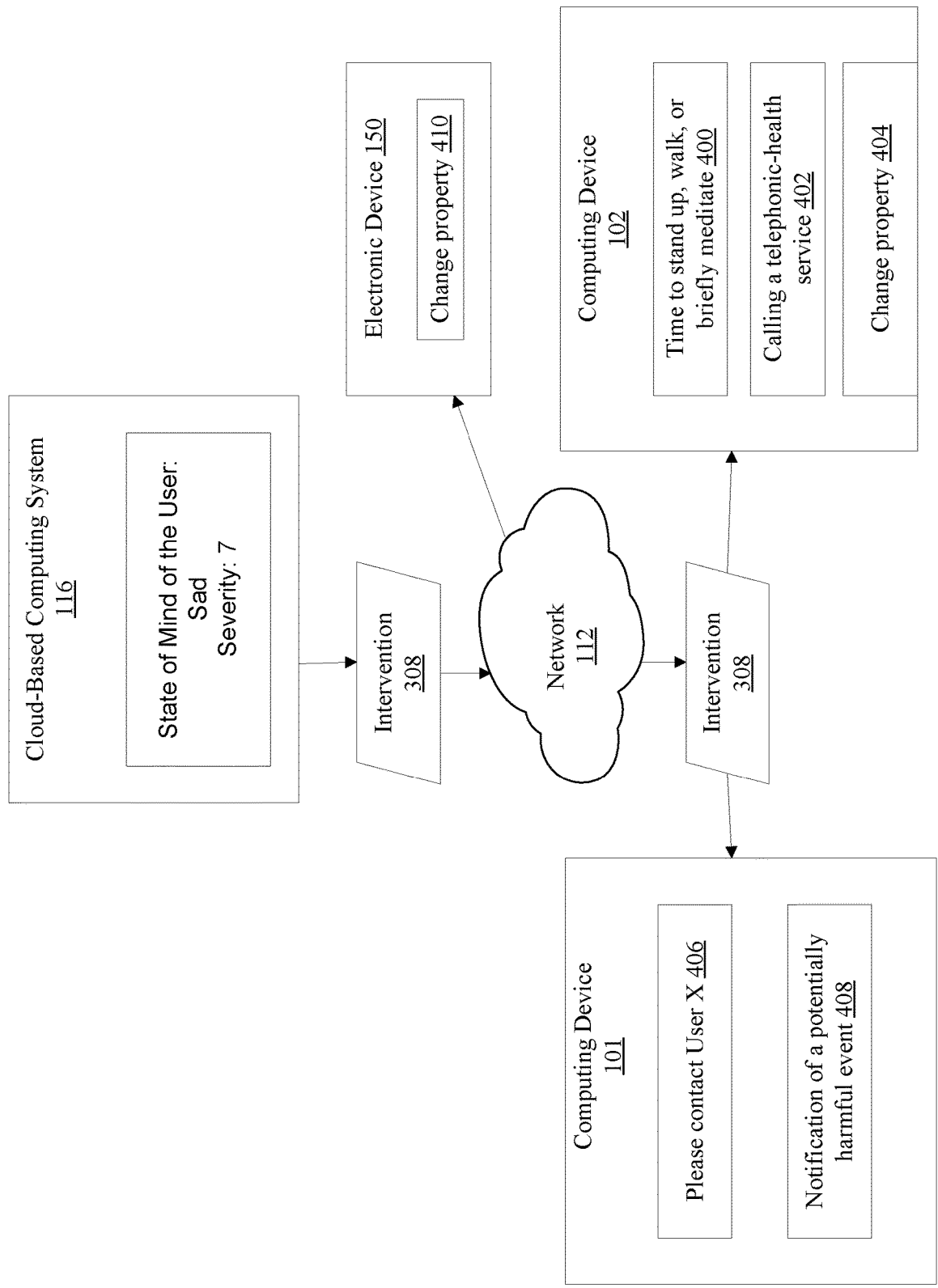
FIG. 4 illustrates an example block diagram of preforming one or more interventions according to certain embodiments of this disclosure.

FIG. 4 illustrates an example block diagram of preforming one or more interventions 308 according to certain embodiments of this disclosure. Continuing with the example described with reference to FIG. 3, where the machine learning models 154 of the cloud-based computing device 116 determined the state of mind of the user is "Sad" and has a severity level of "7". One or more interventions 308 may be performed. For example, the intervention 308 may cause a notification 400 to be presented on the computing device 102 of the user. The notification 400 may instruct the user to stand up, walk, breathe deeply, and/or briefly meditate. Further, the intervention 302 may cause the computing device 102 to connect (e.g., via cellular or WiFi) to a telephonic-health service. In some embodiments, the intervention 308 may change a property (block 404) of the computing device 102. For example, the property change may be a reduction in blue light. Blue light may delay production of melatonin for a certain amount of time (e.g., 4 hours), thus lessening the light may enable the user to fall asleep faster and obtain better rest, which may enhance their mental state.

In some embodiments, the intervention 308 may include causing a notification 406 to be presented on the computing device 101. The notification 406 may recommend that the user of the computing device 101 contacts the user X of the computing device 102. The user of the computing device 101 may be a loved one, family member, sponsor, friend, etc. The notification 406 may cause the user to call, text, email, and/or meet with the user of the computing device 102 to check on how they are feeling. Another intervention 308 may include a notification 408 to a user of the computing device 101. The notification 408 may indicate that a potentially harmful event is about to occur. In some embodiments, notification 408 is transmitted when a major intervention is determined to be performed. The notification 408 may be transmitted to a computing device 101 of an emergency services user.

In some embodiments, the intervention 308 may include changing a property 410 of the electronic device 150. The electronic device 150 may be a smart light, smart home hub, smart thermostat, smart speaker, smart doorbell, and the like. For example, changing the property 410 may include altering a color of light and/or brightness of the light being emitted by the electronic device 150. In some embodiments, the change in property 410 may be causing a smart speaker to play relaxing music, classical music, or any music that is preferred by the user. In some embodiments, the change in property 410 may include lowering a temperature of a smart thermostat to try to cool down the user. Any suitable change in property of an electronic device is contemplated for an intervention 308. It should be understood that the interventions described herein may be performed in real-time as the machine learning models 154 determine the state of mind of the user and/or a severity of the state of mind of the user.

Figure 5:
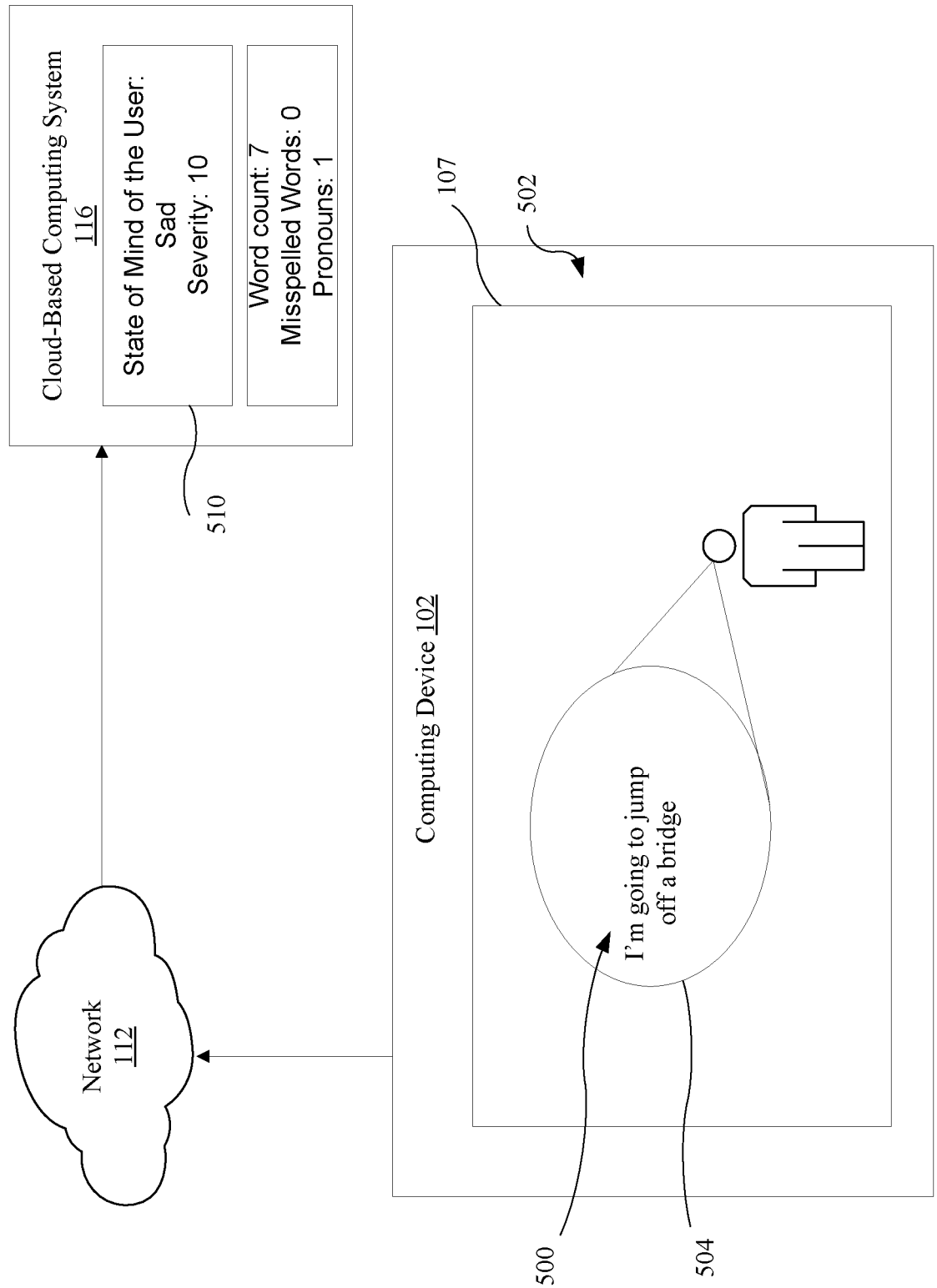
FIG. 5 illustrates an example block diagram of receiving text from spoken words in a video according to certain embodiments of this disclosure.

FIG. 5 illustrates an example block diagram of receiving text 500 from spoken words in a video 502 according to certain embodiments of this disclosure. The video 502 may be playing via the third party application 107, which may be a social media website or any suitable video player application. In the video 502, the user says (in bubble 504) "I'm going to jump off a bridge." The audio of the video may be processed using natural language processing to digitize the string of characters representing words spoken by the user by the cloud-based computing system 116 or the tracking application 111 installed and monitoring the applications running on the computing device 102. Further, facial recognition software may be used to determine an identity of the user that spoke the words in the video 502. If the cloud-based computing system 116 extracts the strings of characters, then the video may be transmitted to the cloud-based computing system 116 for textual extraction. If the tracking application on the computing device 102 extracts the strings of characters, then the strings of characters may be transmitted to the cloud-based computing system 116. In either embodiment, the cloud-based computing system 116 may obtain the strings of characters representing the words spoken in the video 502.

The cloud-based computing system 116 may input the text 500 including the strings of characters into the machine learning models 154. Box 512 shows that the machine learning models 154 determined that the text 500 includes 7 words, 0 misspelled words, and 1 pronoun. The machine learning models 154 may use natural language processing to determine that the substance of the phrase "I'm going to jump off a bridge" is an indication that the user in the video 502 may attempt to hurt their self. Accordingly, the machine learning models 154 may determine that the state of mind of the user is "Sad" and the severity is a maximum level of 10, as shown in box 510.

Figure 6:
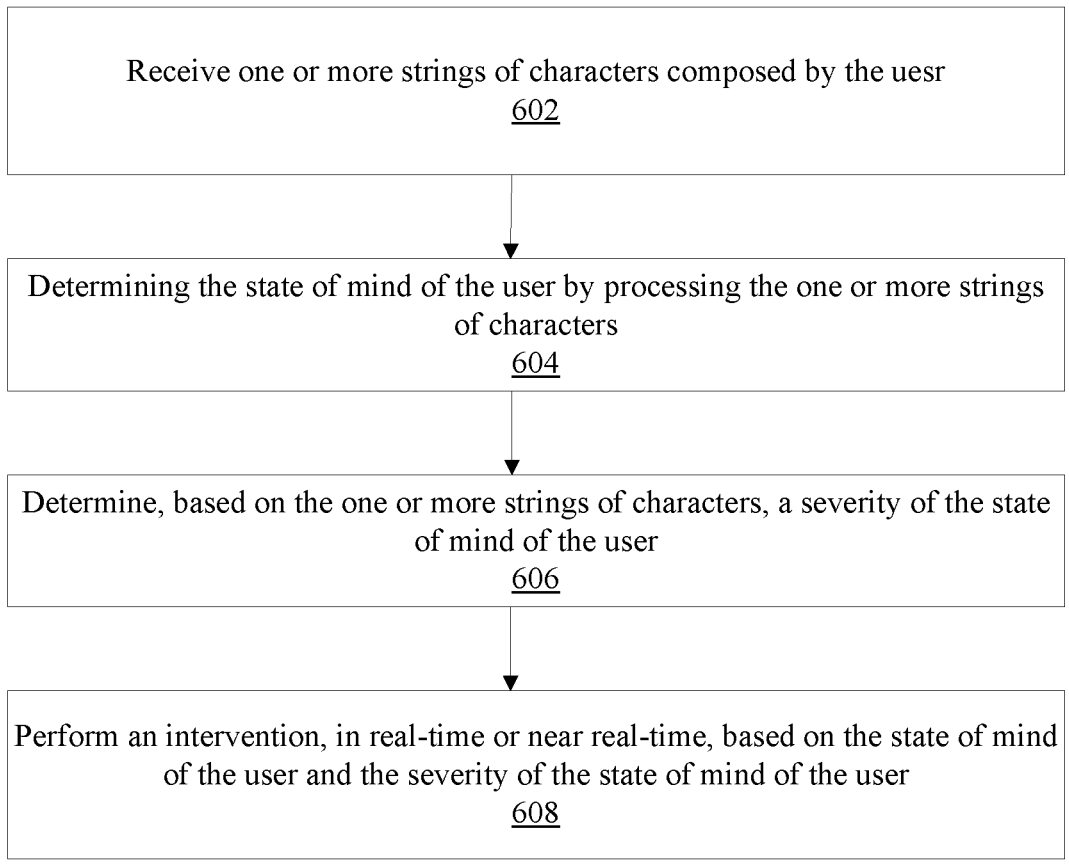
FIG. 6 illustrates example operations of a method for performing an intervention based on a state of mind of a user and a severity of mind of the user according to certain embodiments of this disclosure.

FIG. 6 illustrates example operations of a method 600 for performing an intervention based on a state of mind of a user and a severity of mind of the user according to certain embodiments of this disclosure. The method 600 may be performed by processing logic that may include hardware (circuitry, dedicated logic, etc.), software, or a combination of both. The method 600 and/or each of their individual functions, subroutines, or operations may be performed by one or more processors of a computing device (e.g., any component (server 128, API 135, training engine 152, machine learning models 154, etc.) of cloud-based computing system 116 of FIG. 1) implementing the method 600. The method 500 may be implemented as computer instructions stored on a memory device and executable by the one or more processors. In certain implementations, the method 600 may be performed by a single processing thread. Alternatively, the method 600 may be performed by two or more processing threads, each thread implementing one or more individual functions, routines, subroutines, or operations of the methods.

At block 602, a processing device may receive one or more strings of characters composed by the user. In some embodiments, the strings of characters may be composed by the user in the third party application 107 and/or spoken by the user in a video playing in the third party application 107.

At block 604, the processing device may determine the state of mind of the user by processing the one or more strings of characters. The state of mind may include happy, sad, angry, mad, giddy, playful, silly, anxious, worried, scared, surprised, or some combination thereof. Processing the one or more strings of characters may include using one or more machine learning models trained to determine the state of mind of the user. The machine learning models may be trained using input data (training data) including the other strings of characters composed by other users and feedback from the other users indicating states of mind of the other users when the other users composed the other strings of characters. In some embodiments, the machine learning model may be trained using strings of characters entered by the user and feedback from the user indicating the state of mind of the user and the severity of the state of mind of the user at the time the user composed the strings of characters.

Processing the one or more strings of characters may include identifying similarities of the one or more strings of characters with other strings of characters indicative of the state of mind. Further, processing the one or more strings of characters to determine the state of mind of the user may include determining properties of the strings of characters, such as word count, misspelled words, types of words used, ratios of types of words used relative to other words used, number of pronouns used, gracious and/or celebratory words, derogatory words, angry words, sad words, happy words, and so forth. Further, in some embodiments, the processing device may be communicatively coupled to an electronic medical records system and/or financial system where, provided the user gives consent, the processing device may obtain medical information and/or financial information pertaining to the user. The medical information and/or financial information may also be used to determine the state of mind of the user.

At block 606, the processing device may determine, based on the one or more strings of characters, a severity of the state of mind of the user. The severity may be determined using a scale ranging from one to ten, where one is the least severe level and ten is the most severe level for the state of mind.

At block 608, the processing device may perform an intervention, in real-time or near real-time, based on the state of mind of the user and/or the severity of the state of mind of the user. The intervention may include: (i) causing a color of a display screen of a computing device of the user to be altered, (ii) transmitting a first message to a computing device of a third party, where the first message recommends contacting the user, (iii) causing a prompt to be presented on the computing device of the user, where the prompt recommends the user to stand up, walk, breathe deeply, and/or meditate, (iv) causing the computing device of the user to connect to a telephonic-health service, (v) transmitting a second message to an emergency service, where the second message indicates an event is likely to occur, (vi) causing an electronic device to change a property, or some combination thereof.

The processing device may also track the state of mind and/or the severity of the state of mind of the user over time by monitoring historical states of mind of the user and/or severities of states of mind of the user to determine changes in the state of mind of the user and/or severities of states of mind of the user. If a substantial change (e.g., 2-8 severities levels, occur less than a threshold period of time (e.g., within minutes, hours, days, etc.), then a major intervention may occur. If the changes are subtle over a period of time, then the interventions may increase subtly or decrease subtly over time.

Figure 7:
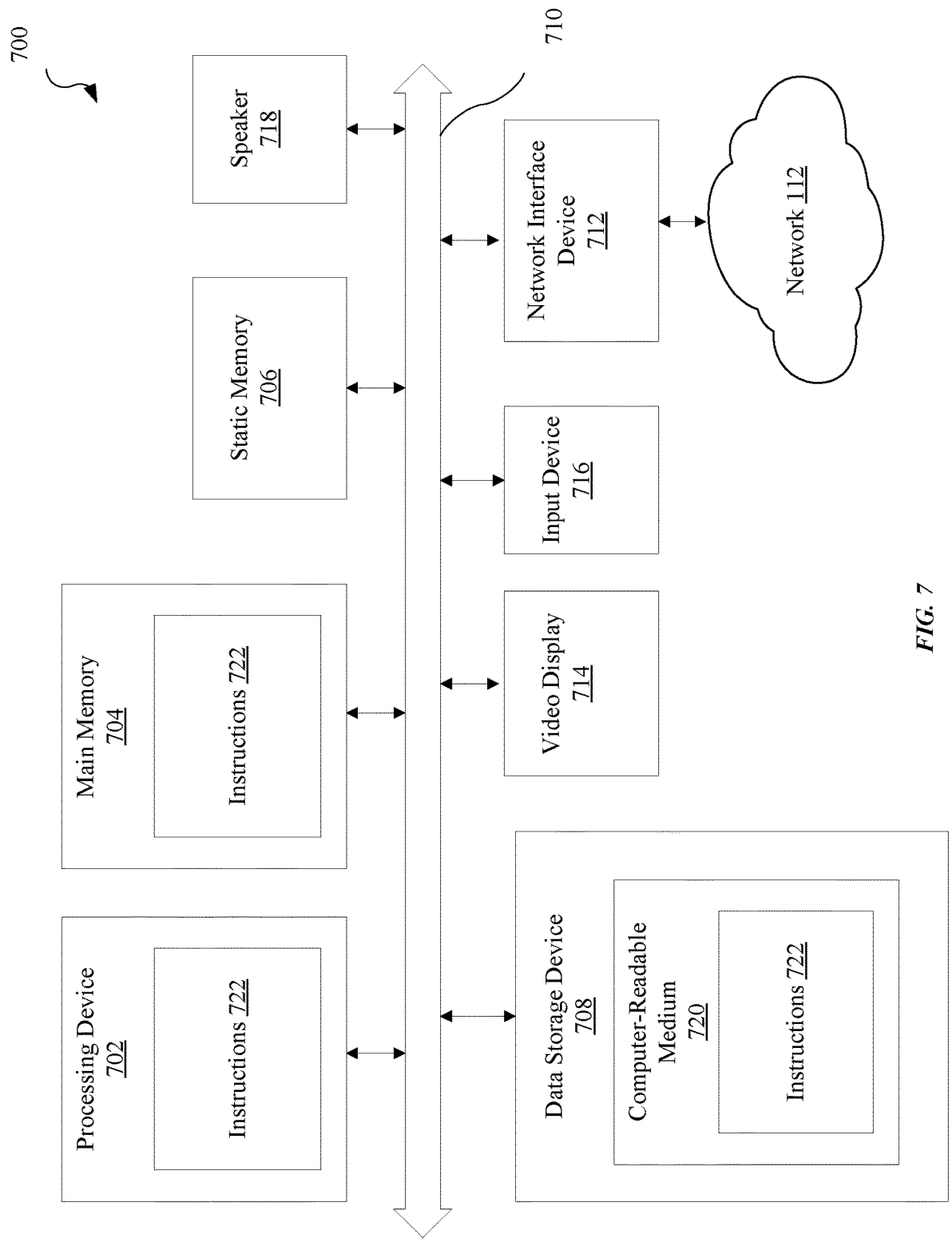
FIG. 7 illustrates an example computer system.

FIG. 7 illustrates an example computer system 700, which can perform any one or more of the methods described herein. In one example, computer system 700 may correspond to the computing device 101, the computing device 102, one or more servers 128 of the cloud-based computing system 116, the electronic device 150, or one or more training engines 152 of the cloud-based computing system 16 of FIG. 1. The computer system 700 may be capable of executing the user interface 105, the tracking application 111, or the third party application 107 of FIG. 1. The computer system 700 may be connected (e.g., networked) to other computer systems in a LAN, an intranet, an extranet, or the Internet. The computer system 700 may operate in the capacity of a server in a client-server network environment. The computer system 700 may be a personal computer (PC), a tablet computer, a laptop, a wearable (e.g., wristband), a set-top box (STB), a personal Digital Assistant (PDA), a smartphone, a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 700 includes a processing device 702, a main memory 704 (e.g., read-only memory (ROM), solid state drive (SSD), flash memory, dynamic random access memory (DRAM) such as synchronous DRAM (SDRAM)), a static memory 706 (e.g., solid state drive (SSD), flash memory, static random access memory (SRAM)), and a data storage device 708, which communicate with each other via a bus 710.

Processing device 702 represents one or more general-purpose processing devices such as a microprocessor, central processing unit, or the like. More particularly, the processing device 702 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 702 may also be one or more special-purpose processing devices such as an application specific integrated circuit (ASIC), a field programmable gate array (FPGA), a digital signal processor (DSP), network processor, or the like. The processing device 702 is configured to execute instructions for performing any of the operations and steps discussed herein.

The computer system 700 may further include a network interface device 712. The computer system 700 also may include a video display 714 (e.g., a liquid crystal display (LCD) or a cathode ray tube (CRT)), one or more input devices 716 (e.g., a keyboard and/or a mouse), and one or more speakers 718 (e.g., a speaker). In one illustrative example, the video display 714 and the input device(s) 716 may be combined into a single component or device (e.g., an LCD touch screen).

The data storage device 716 may include a computer-readable medium 720 on which the instructions 722 (e.g., implementing the application programming interface 135, the user interface 105, the tracking application 111, the third party application 107, and/or any component depicted in the FIGURES and described herein) embodying any one or more of the methodologies or functions described herein are stored. The instructions 722 may also reside, completely or at least partially, within the main memory 704 and/or within the processing device 702 during execution thereof by the computer system 700. As such, the main memory 704 and the processing device 702 also constitute computer-readable media. The instructions 722 may further be transmitted or received over a network via the network interface device 712.

While the computer-readable storage medium 720 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The various aspects, embodiments, implementations or features of the described embodiments can be used separately or in any combination. The embodiments disclosed herein are modular in nature and can be used in conjunction with or coupled to other embodiments, including both statically-based and dynamically-based equipment. In addition, the embodiments disclosed herein can employ selected equipment such that they can identify individual users and auto-calibrate threshold multiple-of-body-weight targets, as well as other individualized parameters, for individual users.

The invention claimed is:

1. A method for determining a state of mind of a user, comprising:
   receiving one or more strings of characters composed by the user;
   determining, by a processing device executing a machine learning model, the state of mind of the user by processing the one or more strings of characters, wherein the processing of the one or more strings of characters comprises identifying similarities of the one or more strings of characters with other strings of characters indicative of the state of mind, and the machine learning model is trained to determine the state of mind of the user using input data comprising:
   (i) the other strings of characters composed by other users, and
   (ii) feedback entered by the other users via user interfaces presented on computing devices of the other users, and the feedback comprises:
      an indication of current states of minds of the other users at the time at which the other users composed the other strings of characters, and
      an indication of severities of the current states of minds of the other users at the time at which the other users composed the other strings of characters; and
   determining, based on the one or more strings of characters, a severity of the state of mind of the user.

2. The method of claim 1, further comprising performing an intervention, in real-time or near real-time, based on the state of mind of the user and the severity of the state of mind of the user.

3. The method of claim 2, wherein the intervention comprises:
   causing a color of a display screen of a computing device of the user to be altered;
   transmitting a first message to a computing device of a third party, wherein the first message recommends contacting the user;
   causing a prompt to be presented on the computing device of the user, wherein the prompt recommends the user stand up, walk, or briefly meditate;
   causing the computing device of the user to connect to a telephonic-health service;
   transmitting a second message to an emergency service, wherein the second message indicates an event is likely to occur;
   causing an electronic device to change a property; or
   some combination thereof.

4. The method of claim 1, wherein the state of mind is happy or sad.

5. The method of claim 1, wherein the severity is determined using a scale ranging from one to ten, one being least severe and ten being most severe.

6. The method of claim 1, further comprising tracking the state of mind of the user over time by monitoring historical states of mind of the user to determine changes in the state of mind of the user.

7. A tangible, non-transitory computer-readable medium storing instructions that, when executed by a processing device, cause the processing device to:
   receive one or more strings of characters composed by the user;
   determine, by a processing device executing a machine learning model, the state of mind of the user by processing the one or more strings of characters, wherein the processing of the one or more strings of characters comprises identifying similarities of the one or more strings of characters with other strings of characters indicative of the state of mind, and the machine learning model is trained to determine the state of mind of the user using input data comprising:
   (i) the other strings of characters composed by other users, and
   (ii) feedback entered by the other users via user interfaces presented on computing devices of the other users, and the feedback comprises:
      an indication of current states of minds of the other users at the time at which the other users composed the other strings of characters, and
      an indication of severities of the current states of minds of the other users at the time at which the other users composed the other strings of characters; and
   determine, based on the one or more strings of characters, a severity of the state of mind of the user.

8. The computer-readable medium of claim 7, wherein the processing device is further to perform an intervention based on the state of mind of the user and the severity of the state of mind of the user.

9. The computer-readable medium of claim 8, wherein the intervention comprises:
   causing a color of a display screen of a computing device of the user to be altered;

transmitting a first message to a computing device of a third party, wherein the first message recommends contacting the user;

causing a prompt to be presented on the computing device of the user, wherein the prompt recommends the user stand up, walk, or briefly meditate;

causing the computing device of the user to connect to a telephonic-health service;

transmitting a second message to an emergency service, wherein the second message indicates an event is likely to occur;

causing an electronic device to change a property; or some combination thereof.

10. The computer-readable medium of claim 7, wherein the state of mind is happy or sad.

11. The computer-readable medium of claim 7, wherein the severity is determined using a scale ranging from one to ten, one being least severe and ten being most severe.

12. The computer-readable medium of claim 7, further comprising tracking the state of mind of the user over time by monitoring historical states of mind of the user to determine changes in the state of mind of the user.

13. A system, comprising:
a memory device storing instructions;
a processing device communicatively coupled to the memory device, wherein the processing device executes the instructions to:
receive one or more strings of characters composed by the user;
determine, by a processing device executing a machine learning model, the state of mind of the user by processing the one or more strings of characters, wherein the processing of the one or more strings of characters comprises identifying similarities of the one or more strings of characters with other strings of characters indicative of the state of mind, and the machine learning model is trained to determine the state of mind of the user using input data comprising:
(i) the other strings of characters composed by other users, and
ii feedback entered by the other users via user interfaces presented on computing devices of the other users, and the feedback comprises:
an indication of current states of minds of the other users at the time at which the other users composed the other strings of characters, and
an indication of severities of the current states of minds of the other users at the time at which the other users composed the other strings of characters; and
determine, based on the one or more strings of characters, a severity of the state of mind of the user.

14. The system of claim 13, wherein the processing device is further to perform an intervention based on the state of mind of the user and the severity of the state of mind of the user.

15. The system of claim 13, wherein the intervention comprises:
causing a color of a display screen of a computing device of the user to be altered;
transmitting a first message to a computing device of a third party that recommends contacting the user;
causing a prompt to be presented on the computing device of the user, wherein the prompt recommends the user stand up, walk, or briefly meditate;
causing the computing device of the user to connect to a telephonic-health service;
transmitting a second message to an emergency service, wherein the second message indicates an event is likely to occur;
causing an electronic device to change a property; or
some combination thereof.

16. The method of claim 1, further comprising:
determining whether the state of mind of the user satisfies a threshold level; and
responsive to determining the state of mind of the user satisfies the threshold level, performing an intervention corresponding to the threshold level.

17. The method of claim 1, further comprising:
determining a difference in the severity of the state of mind of the user and a previously determined severity of the state of mind of the user;
determining whether the difference satisfies a threshold; and
responsive to determining the difference satisfies the threshold, performing an intervention based at least on one or more of the state of mind of the user, the severity of the state of mind of the user, and the difference.

* * * * *